(12) United States Patent
Yoo et al.

(10) Patent No.: US 11,034,801 B2
(45) Date of Patent: Jun. 15, 2021

(54) TRANSPARENT HYDROGEL MEMBRANE INCLUDING HYALURONIC ACID, AND CONTACT LENS INCLUDING SAME

(71) Applicant: JCBIO CO., LTD., Seoul (KR)

(72) Inventors: Jae Chan Yoo, Gyeonggi-do (KR); Yoo Lee Kang, Seoul (KR); Min Young Kong, Seoul (KR)

(73) Assignee: JCBIO CO., LTD., Seoul (KR)

( * ) Notice: Subject to any disclaimer, the term of this patent is extended or adjusted under 35 U.S.C. 154(b) by 0 days.

(21) Appl. No.: 16/648,053

(22) PCT Filed: Sep. 18, 2018

(86) PCT No.: PCT/KR2018/011002
§ 371 (c)(1),
(2) Date: Mar. 17, 2020

(87) PCT Pub. No.: WO2019/054850
PCT Pub. Date: Mar. 21, 2019

(65) Prior Publication Data
US 2020/0262985 A1 Aug. 20, 2020

(30) Foreign Application Priority Data

Sep. 18, 2017 (KR) .......................... 10-2017-0119492

(51) Int. Cl.
*C08J 3/075* (2006.01)
*G02C 7/04* (2006.01)
(Continued)

(52) U.S. Cl.
CPC ............... *C08J 3/075* (2013.01); *A61K 47/36* (2013.01); *B29D 11/00096* (2013.01);
(Continued)

(58) Field of Classification Search
CPC ...... A61K 9/0051; A61K 47/36; A61K 45/06; C08J 2205/022; C08J 3/075;
(Continued)

(56) References Cited

U.S. PATENT DOCUMENTS

2006/0142191 A1\* 6/2006 Francois .............. C07K 14/005
514/3.7
2009/0155362 A1\* 6/2009 Longin .................. A61K 45/06
424/484

FOREIGN PATENT DOCUMENTS

CN 104327311 A \* 2/2015
JP 4006039 B2 11/2007
(Continued)

OTHER PUBLICATIONS

Mohammed Abdullah Al-Sibani, Enhancement of cross-linking efficiency of hyaluronic acid-based hydrogels cross-linked with 1 4-butanediol diglycidyl ether, A comparative evaluation of different method conditions, May 17, 2017.
A picture of a prototype corresponding to Korean Patent Application No. 10-2017-0119492.
(Continued)

*Primary Examiner* — Jianfeng Song
(74) *Attorney, Agent, or Firm* — IP & T Group LLP

(57) ABSTRACT

The present invention provides a method for preparing a transparent hydrogel membrane, the method including: (a) preparing 6 to 10 wt % of a hyaluronic acid solution based on a total weight of a mixture by dissolving a hyaluronic acid in a basic aqueous solution; (b) mixing, with the hyaluronic acid solution, 0.01 to 0.05 wt % of a crosslinking agent based on the total weight of the mixture; and (c) shaping the transparent hydrogel membrane by pouring the mixture into a mold.

1 Claim, 3 Drawing Sheets

(51) Int. Cl.
*G02B 1/04* (2006.01)
*A61K 47/36* (2006.01)
*C08J 3/24* (2006.01)
*B29D 11/00* (2006.01)
*A61K 9/00* (2006.01)
*A61K 45/06* (2006.01)

(52) U.S. Cl.
CPC ................ *C08J 3/24* (2013.01); *G02B 1/043* (2013.01); *G02C 7/04* (2013.01); *A61K 9/0051* (2013.01); *A61K 45/06* (2013.01); *C08J 2305/08* (2013.01)

(58) Field of Classification Search
CPC .......... C08J 2305/08; C08J 3/24; C08J 3/247; C08L 5/08; C08L 2203/02; B29D 11/00096; G02B 1/043; G02C 7/04
See application file for complete search history.

(56) References Cited

FOREIGN PATENT DOCUMENTS

| | | |
|---|---|---|
| JP | 2016-118797 A | 6/2016 |
| JP | 2017-505922 A | 2/2017 |
| KR | 10-2007-0004159 A | 1/2007 |
| KR | 10-2010-0079523 A | 7/2010 |
| KR | 10-2010-0118102 A | 11/2010 |
| KR | 10-1382083 B1 | 4/2014 |
| KR | 10-2016-0060227 A | 5/2016 |
| KR | 10-1724984 B1 | 4/2017 |
| KR | 10-1775358 B1 | 9/2017 |

OTHER PUBLICATIONS

How to use and care for a contact lens for treatment, the manufacture date of a contact lens for treatment, Oct. 17, 2017, www.jcbio.co.kr.

* cited by examiner

TRANSPARENT HYDROGEL MEMBRANE INCLUDING HYALURONIC ACID, AND CONTACT LENS INCLUDING SAME

TECHNICAL FIELD

The present invention relates to a method for preparing a transparent hydrogel membrane in which hyaluronic acid is copolymerized by a crosslinking agent, a transparent hydrogel membrane prepared by the method, and a contact lens using the same.

BACKGROUND ART

Hyaluronic acid (HA) is one of the most widely used biocompatible polymers for medical use. Hyaluronic acid is a polymer consisting of two sugars, glucuronic acid and N-acetylglucosamine. Hyaluronic acid is a natural mucopolysaccharide that is widely distributed in the interstices of tissues, is present in a large amount in the synovial fluid, cartilage, skin, eyeballs, and the like of a human, serves as a three-dimensional crosslinker of intercellular molecules, and protects cartilages between the cartilages due to its high viscosity. Further, hyaluronic acid contains a large amount of carboxyl groups, which is a hydrophilic group, and thus has a feature that its mechanical strength is reduced when it comes into contact with moisture.

In general, hyaluronic acid plays a positive role in cell culture, promotes the regeneration of corneal epithelial cells, and is used as a viscosupplement, a drug, and a surgical adjuvant, such as being used as a main material of artificial tears for treating ocular surface diseases in the ophthalmic field. Such long-term clinical application of hyaluronic acid has already secured safety in the eyeballs. In addition, hyaluronic acid has been extensively tested in viscosupplementation to relieve articular pain caused by osteoarthritis of different natures as a lubricant administered by intra-articular injections.

A hydrogel is a representative material of soft contact lenses used by modern people for vision correction and treatment purposes. Most hydrogel contact lenses employ 2-hydroxyethyl methacrylate (HEMA) as a main material.

A hydrogel has a three-dimensional network structure, can contain a large amount of water, and has biocompatibility due to excellent hydrophilicity. In particular, a hydrogel including natural polymers is biocompatible and excellent in biodegradability, and thus has been widely used as a drug carrier. A hydrogel has high hygroscopicity, stability and non-toxicity, and show excellent biocompatibility when contacting blood, body fluids and the living body. A hydrogel consists of natural polymers or derivatives thereof, synthetic polymers, or a combination of natural and synthetic polymers, their molecules interacting with one another through electrostatic forces or chemical bonds form hydrophilic cross-linked polymers and can absorb water in an amount ranging from 10 to 20% to several hundred times its dry weight. In particular, a hydrogel is an ideal candidate material for the manufacture of a tissue engineering substrate for the purpose of healing or reconstituting damaged or diseased or degenerated human tissues and organs.

Contact lenses have been widely used because they are convenient to wear on the eyes. Such contact lenses are generally susceptible to contamination by proteins or fats transmitted from the fingers, or proteins of tears. When such contaminants are attached in a large amount, not only the effect of enhancing visual acuity by the contact lens greatly deteriorates, but also discomfort is increased as if foreign matter is entering the eyes, by the contact lens. Therefore, there has been a constant need for an eye protection contact lens improve these problems.

Throughout the present specification, a plurality of papers and patent documents are referenced, and citations thereof are indicated. The disclosure of each of the cited papers and patent documents is incorporated herein by reference in its entirety to describe the level of the technical field to which the present invention pertains and the content of the present invention more clearly.

DISCLOSURE

Technical Problem

The present invention relates to a transparent hydrogel membrane formed by copolymerizing hyaluronic acid through a crosslinking agent and a transparent contact lens prepared using the same, and is intended to provide a transparent contact lens which exhibits excellent transparency, flexibility, and sustained release of drug.

Technical Solution

A method for preparing a transparent hydrogel membrane according to an embodiment of the present invention includes: (a) preparing 6 to 10 wt % of a hyaluronic acid solution based on a total weight of a mixture by dissolving a hyaluronic acid in a basic aqueous solution; (b) mixing, with the hyaluronic acid solution, 0.01 to 0.05 wt % of a crosslinking agent based on the total weight of the mixture; and (c) shaping the transparent hydrogel membrane by pouring the mixture into a mold.

Specifically, the crosslinking agent may be selected from the group consisting of butanediol diglycidyl ether (BDDE), 1-ethyl-3-(3-dimethylaminopropyl)carbodiimide (EDC), diepoxyoctane, 1,2-bis-(2,3-epoxypropyl)-2,3-ethylene, and a combination thereof.

Another embodiment of the present invention provides a transparent hydrogel membrane prepared by the method.

Specifically, the transparent hydrogel membrane may have an oxygen permeability of 10,000 cm$^3$/m$^2$·24 hr·atm or more in accordance with the ASTM D3985 standard.

Specifically, the transparent hydrogel membrane may have a visible light transmittance of 90 to 95%.

Specifically, the transparent hydrogel membrane may further include a drug selected from the group consisting of an antiphlogistic agent, an analgesic agent, an epithelial regeneration promoter, an anesthetic agent, a hemostatic agent, an antimicrobial agent, an antibacterial agent, an antiviral agent, an antifungal agent, an antiinflammatory agent, an antioxidant, an antiseptic agent, an antihistamine agent, an antipruritic agent, an antipyretic agent, an immunostimulator, a dermatological preparation, an anticancer agent, and a combination thereof.

Still another embodiment of the present invention provides a contact lens for preventing or treating an ophthalmic disease, including the transparent hydrogel membrane.

Advantageous Effects

The contact lens according to the present invention provides a crosslinked hyaluronic acid hydrogel membrane with improved transparency, flexibility, and the like, which has excellent biocompatibility, is effective for wound healing and inflammation treatment, and can be applied as amnionic membrane substitutes for treating ocular surface diseases such as corneal injury.

Further, a drug can be slowly released below a certain rate by a crosslinked product in the hydrogel membrane, and through the drug of the hydrogel membrane, it is possible to exhibit additional effects such as suppression of inflammation, regulation of pain, and promotion of epithelial regeneration.

MODES OF THE INVENTION

Figure 1A:
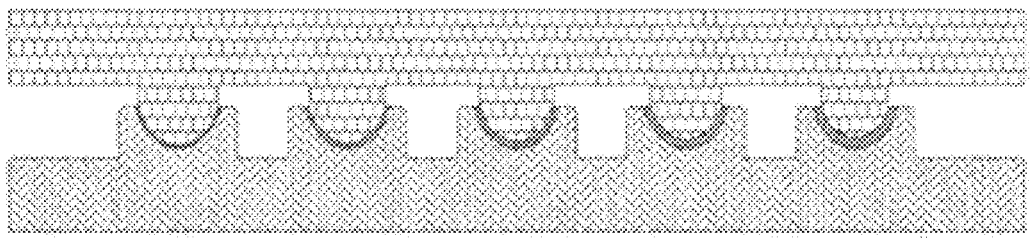
FIG. 1A illustrates a mold preparing a transparent contact lens formed by copolymerizing the hyaluronic acid according to the present invention.

An aspect of the present invention provides a transparent hydrogel membrane formed by copolymerizing by a hyaluronic acid and a crosslinking agent.

As used herein, the term "hyaluronic acid" is present in the ocular vitreous body or umbilical cord, and the like in the human body, is highly viscous, and plays an important role in preventing the invasion of bacteria and the penetration of toxic substances. In the present invention, the hyaluronic acid may be preferably a low molecular weight hyaluronic acid, more preferably an 800,000 to 1,200,000 dalton hyaluronic acid. The hyaluronic acid may be included in an amount of 6 to 10 wt %, for example, 8 wt % based on the weight of the entire hydrogel membrane.

As used herein, the term "crosslinking agent" serves to link and copolymerize hyaluronic acid monomers, and an internal structure of the transparent hydrogel membrane may form a network structure by the copolymerization. The crosslinking agent may be generally different types of bi- or multi-functional crosslinking agents, and may be, for example, selected from the group consisting of divinyl sulfone, bi- or multi-functional epoxides, carbodiimides, and formaldehydes, but is not limited thereto. The crosslinking agent may be preferably an agent selected from the group consisting of bi- or multi-functional epoxides, more preferably 1,4-butanediol diglycidyl ether (BDDE), 1-ethyl-3-(3-dimethylaminopropyl)carbodiimide (EDC), diepoxyoctane, 1,2-bis-(2,3-epoxypropyl)-2,3-ethylene, or a combination thereof, and even more preferably 1,4-butanediol diglycidyl ether or 1-ethyl-3-(3-dimethylaminopropyl)carbodiimide. The 1,4-butanediol diglycidyl ether has a molecular weight of 202.25, and compensates for a disadvantage of rapid degradation by crosslinking hyaluronic acid which has a short half-life to form a hydrogel. The crosslinking agent may be included in an amount of 0.01 to 0.05 wt % based on the weight of the entire hydrogel membrane. When the content of the crosslinking agent is less than 0.01 wt %, the formation of a membrane, which maintains the curvature of the lens, may not be achieved, and when the content is more than 0.05 wt %, the blending of the membrane formation may be performed well, but the lens may not be transparent, and the water content may be excessively high.

The transparent hydrogel membrane may further include, for example, a drug selected from the group consisting of an antiphlogistic agent, an analgesic agent, an epithelial regeneration promoter, an anesthetic agent, a hemostatic agent, an antimicrobial agent, an antibacterial agent, an antiviral agent, an antifungal agent, an antiinflammatory agent, an antioxidant, an antiseptic agent, an antihistamine agent, an antipruritic agent, an antipyretic agent, an immunostimulator, a dermatological preparation, an anticancer agent, and a combination thereof, but the drug is not limited thereto. The drug further included in the transparent hydrogel membrane may assist wound healing or enhance an effect of wound healing.

The transparent hydrogel membrane may be used for preventing or treating an opthalmic condition, for example, various ocular conditions such as xerophthalmia, keratitis, glaucoma, uveitis, ocular inflammation, allergies, ocular infections, carcinoma, corneal neovascularization, retinal edema, macular edema, diabetic retinopathy, retinopathy of prematurity, retinal degenerative diseases (macular degeneration, retinal dystrophy), and retinal diseases associated with glial proliferation, but the ophthalmic condition is not limited thereto.

An aspect of the present invention provides a contact lens for preventing or treating an opthalmic disease, which includes the transparent hydrogel membrane, preferably prepared by the transparent hydrogel membrane.

An aspect of the present invention provides a method for preparing a transparent hydrogel membrane, the method including: (a) preparing a hyaluronic acid solution by dissolving hyaluronic acid in a basic aqueous solution with a pH of 8; (b) mixing a crosslinking agent with the mixed solution; and (c) gelling the mixture and shaping the transparent hydrogel membrane by pouring the mixture into a mold. In this case, the hyaluronic acid may be contained in an amount of 6 to 10 wt %, for example, 8 wt % based on the weight of the mixture, and the crosslinking agent may be contained in an amount of 0.01 to 0.05 wt % based on the weight of the mixture.

As used herein, the term "basic aqueous solution" may be an aqueous solution of a hydroxide of an alkali metal or a hydroxide of an alkaline earth metal, for example, an aqueous solution of lithium hydroxide, sodium hydroxide, potassium hydroxide, magnesium hydroxide, beryllium hydroxide, calcium hydroxide, or a combination thereof, but is not limited thereto. An aqueous solution of sodium hydroxide may be easy in terms of pH control and concentration control.

Hereinafter, the present invention will be described in more detail through one or more Examples. However, these Examples are provided only for exemplarily explaining the present invention, and the scope of the present invention is not limited by these Examples.

Preparation Example 1. Manufacture of Mold

Figure 1B:
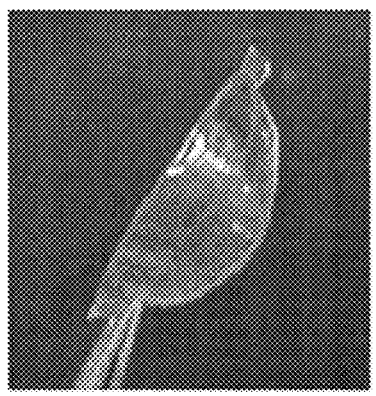
FIGS. 1B and 1C illustrate transparent contact lenses formed through the mold according to the present invention.
Figure 1C:
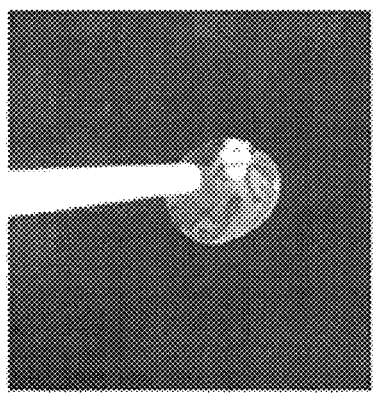

In order to prepare a hyaluronic acid contact lens according to the present invention, a mold was manufactured using a polycarbonate (PC) made of a transparent material such that a process of forming the lens could be confirmed (FIG. 1).

The mold consisted of an upper jig front cover and a lower jig rear base, and in order to observe the diversity according to the size which varied depending on use, when the upper front cover was assembled with the lower rear base, the mold was processed using a machining center (MCT) to divide the interval into five types such as 0.5 mm, 1 mm, 1.5 mm, 2 mm, and 2.5 mm.

The following Examples were designed for the purpose of testing the diversity when hyaluronic acid contact lenses having different thicknesses are manufactured according to the interval between the upper and lower jigs, in the molding of contact lenses. In order to secure a precise-dimensional interval during the assembly of the mold, the contact surface of a fixing SUS PIN press-fitted to both ends of the jig was used. Fastening was performed using M4 bolts on the center tab of the SUS PIN.

The mold has a structure in which during the preparation of a contact lens, an excess mixture flows to a lower portion of the mold when the capacity exceeds an allowable capacity at an interval between upper and lower jigs.

Examples 1: Preparation of Hyaluronic Acid Contact Lens

A uniform hyaluronic acid mixture was prepared by dissolving non-crosslinked hyaluronic acid in an amount of 8 wt % in an aqueous sodium hydroxide solution with a pH of 8 and adding 0.01 wt % of BDDE thereto. The hyaluronic acid mixture was poured into a polycarbonate mold prepared in Preparation Example 1 and dried in an oven at 40° C. for 30 hours. Hyaluronic acid contact lenses of a predetermined size prepared by drying the hyaluronic acid mixture were washed three times in total with distilled water every 24 hours, and after a washing process of 72 hours was performed, a hyaluronic acid hydrogel film was obtained. The hyaluronic acid hydrogel membrane had a diameter of 9 mm and a thickness of 20 μm in size.

Examples 2 to 7: Preparation of Hyaluronic Acid Contact Lens

Hyaluronic acid hydrogel membranes were prepared in the same manner as described in Example 1, except that the amount of BDDE used was changed as shown in the following Table 1.

TABLE 1

|  | Example 2 | Example 3 | Example 4 | Example 5 | Example 6 | Example 7 |
|---|---|---|---|---|---|---|
| Hyaluronic acid (wt %) | 8 | 8 | 8 | 6 | 10 | 10 |
| BDDE (wt %) | 0.02 | 0.03 | 0.05 | 0.03 | 0.01 | 0.03 |
| Aqueous NaOH solution | Remainder | Remainder | Remainder | Remainder | Remainder | Remainder |
| Total | 100 | 100 | 100 | 100 | 100 | 100 |

Comparative Examples 1 to 5. Preparation of Hyaluronic Acid Contact Lens

Hyaluronic acid hydrogel membranes were prepared in the same manner as described in Example 1, except that the amount of BDDE used was changed as shown in the following Table 2.

TABLE 2

|  | Comparative Example 1 | Comparative Example 2 | Comparative Example 3 | Comparative Example 4 | Comparative Example 5 |
|---|---|---|---|---|---|
| Hyaluronic acid (wt %) | 8 | 8 | 8 | 6 | 10 |
| BDDE (wt %) | 0.005 | 0.07 | 0.1 | 0.07 | 0.07 |
| Aqueous NaOH solution | Remainder | Remainder | Remainder | Remainder | Remainder |
| Total | 100 | 100 | 100 | 100 | 100 |

Experimental Example 1. Evaluation of Water Content of Hyaluronic Acid Contact Lens In order to evaluate the water content of the hyaluronic acid contact lens prepared in Example 1, the contact lens was immersed in PBS at 37° C. for 24 hours, and then a change in the ratio of the sample mass after immersion compared to the initial sample mass was observed.

Figure 2:
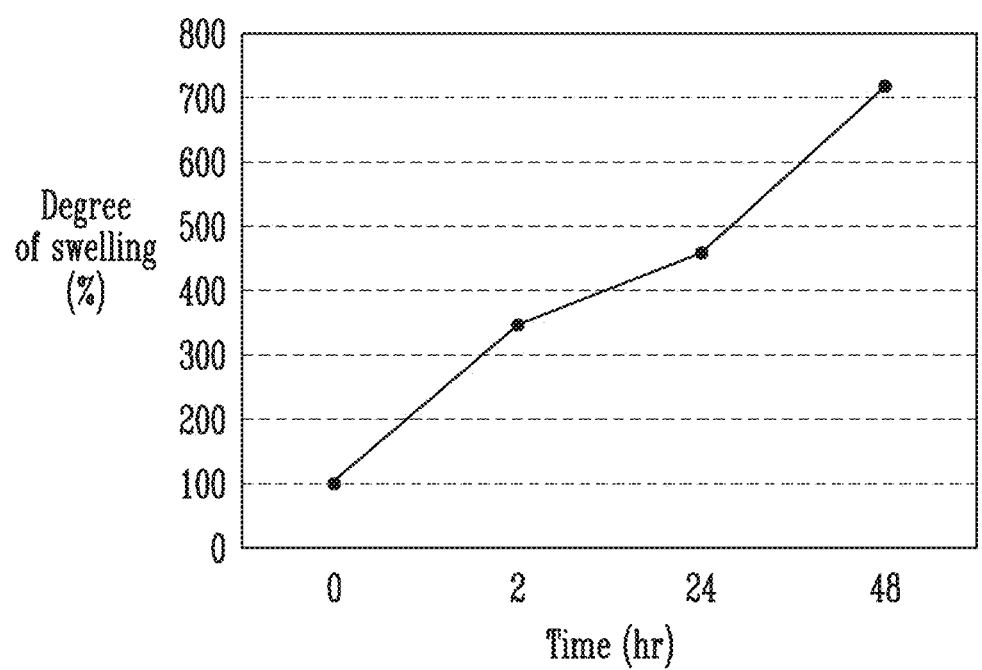
FIG. 2 illustrates the degree of swelling of the transparent contact lens according to the present invention over the swelling time.

As a result of the experiment, it was confirmed that the weight of the contact lens after immersion increased 4.5-fold compared to the initial weight (that is, the water content was 350%) (FIG. 2).

Experimental Example 2. Evaluation of Oxygen Permeability of Hyaluronic Acid Contact Lens The oxygen permeability of the hyaluronic acid contact lens prepared in Example 1 was evaluated. The test method was performed in accordance with the ASTM D3985 standard, and the temperature condition and the measurement range were set to 23±2° C. and 0.05 to 10,000 $cm^3/m^2 \cdot 24$ hr·atm, respectively.

As a result of the experiment, it was confirmed that the hyaluronic acid contact lens prepared in Example 1 had an excellent oxygen permeability of 10,000 $cm/m^2 \cdot 24$ hr·atm or more on average.

Experimental Example 3. Evaluation of Visible Light Transmittance of Hyaluronic Acid Contact Lens In order to evaluate the visible light transmittance of the hyaluronic acid contact lens prepared in Example 1, the visible light transmittance of the contact lens was measured in a wavelength range of 200 to 1,100 nm under a transmission mode air condition of a UV-VIS spectrophotometer.

Figure 3:
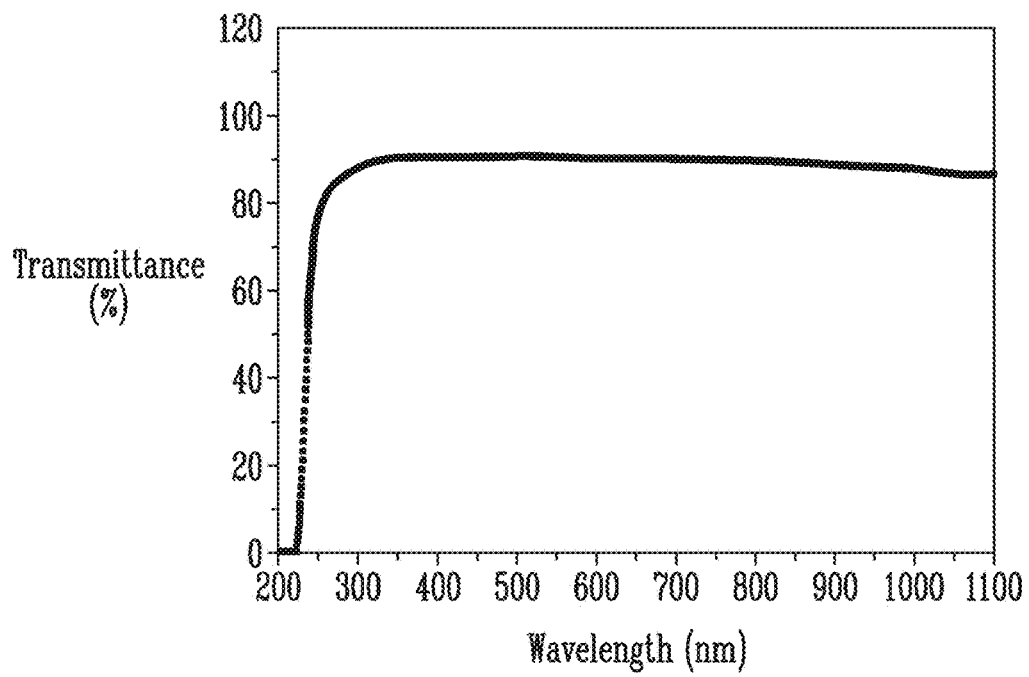
FIG. 3 illustrates the visible light transmittance of the transparent contact lens according to the present invention.

As a result of the experiment, it was confirmed that the hyaluronic acid contact lens prepared in Example 1 had an excellent visible light transmittance of 92% on average (FIG. 3).

Experimental Example 4. Evaluation of Toxicity of Hyaluronic Acid Hydrogel 4.1. Cell Culture HeLa cells (CCL-2) purchased from the American Type Culture Collection (ATCC, Manassas, Va., USA) were resuspended in a HeLa cell basal medium in a proliferation kit provided by the ATCC. After cells were inoculated into a 75 cm$^2$ tissue culture flask, air was maintained at 37° C., 5% $CO_2$ and 95% humidity. The culture medium was changed every three days, treat the cells with 0.05% trypsin-EDTA (Gibco BRL, CA, USA), and the cells with a subculture number of 5 or less were used in the present experimental example.

4.2. Hydrogel Treatment and Cell Viability Analysis

In order to evaluate the toxicity of the hyaluronic acid contact lens prepared in Example 1, an MTT analysis was performed.

In short, HeLa cells were cultured in 96-well plates at a concentration of 1×10$^4$ cells/well 24 hours prior to treatment with a contact lens eluate. After the contact lens prepared in Example 1 was swollen in a cell medium for 24 hours, 1 mL of the eluate was added to each well in which 1 mL of the culture medium was distributed (as a control, 2 mL of a culture medium was used without adding the eluate), and then cultured at 37° C. for 1 hour, 2 hours, 6 hours, and 24 hours, respectively. Thereafter, 10 µl of an MTT tetrazolium reagent was added to each well, and the absorbance at 450 nm was measured 2 hours after the culture with the MTT tetrazolium reagent.

Figure 4:
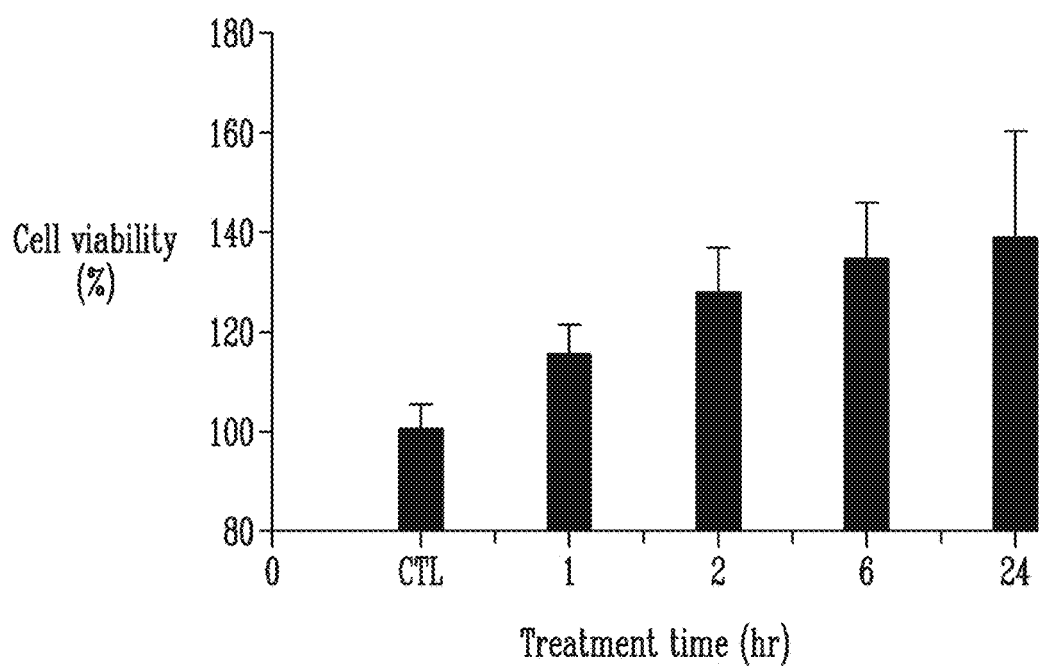
FIG. 4 illustrates the results of cytotoxicity evaluation over the treatment time of the eluate of the transparent contact lens according to the present invention.

As a result of the experiment, it was confirmed that the viability of cells was gradually increased in proportion to the eluate treatment time (see FIG. 4), and through this, it was confirmed that the eluate of the contact lens was not toxic to cells.

Table 3 below shows the experimental results of the Examples and Comparative Examples including Example 1.

From the foregoing, the present invention has been reviewed mainly based on the preferred examples thereof. A person with ordinary skill in the art to which the present invention pertains will be able to understand that the present invention may be implemented in a modified form without departing from the essential characteristics of the present invention. Therefore, the disclosed examples should be considered not from a restrictive viewpoint, but from an explanatory viewpoint. The scope of the present invention is represented by the claims to be described below rather than the foregoing detailed description, and it should be interpreted that the meaning and scope of the claims and all the changes or modified forms derived from the equivalent concepts thereto fall within the scope of the present invention.

The invention claimed is:

1. A method for preparing a transparent hydrogel membrane, the method comprising:
   (a) preparing 6 to 10 wt % of a hyaluronic acid solution based on a total weight of a mixture by dissolving a hyaluronic acid in a basic aqueous solution;
   (b) mixing, with the hyaluronic acid solution, 0.01 to 0.05 wt % of a crosslinking agent based on the total weight of the mixture; and
   (c) shaping the transparent hydrogel membrane by pouring the mixture into a mold,
   wherein the hyaluronic acid has a molecular weight of from 800,000 to 1,200,000 Dalton units, and

TABLE 3

| | Example 1 | Example 2 | Example 3 | Example 4 | Example 5 | Example 6 |
|---|---|---|---|---|---|---|
| Water content (%) | 350 | 363 | 380 | 405 | 400 | 300 |
| Oxygen permeability (cm$^3$/m$^2$ · 24 hr · atm) | 10,000 or more | 10,000 or more | 10,000 or more | 10,000 or more | 10,000 or more | 10,000 or more |
| Apparent transparency | Transparent | Transparent | Transparent | Transparent | Transparent | Transparent |
| Visible light Transmittance (%) | 92 | 92 | 90 | 88 | 90 | 93 |
| Toxicity evaluation | Good | Good | Good | Good | Good | Good |

| | Example 7 | Comparative Example 1 | Comparative Example 2 | Comparative Example 3 | Comparative Example 4 | Comparative Example 5 |
|---|---|---|---|---|---|---|
| Water content (%) | 360 | — | 500 | 750 | 720 | 460 |
| Oxygen permeability (cm$^3$/m$^2$ · 24 hr · atm) | 10,000 or more | Cannot be measured | 10,000 or more | 10,000 or more | 10,000 or more | 10,000 or more |
| Apparent transparency | Transparent | Membrane formation X | Semi-transparent | Semi-transparent | Semi-transparent | Semi-transparent |
| Visible light Transmittance (%) | 91 | Cannot be measured | 80 | 73 | 70 | 82 |
| Toxicity assessment | Good | Cannot be measured | Good | Good | Good | Good | wherein the crosslinking agent is butanediol diglycidyl ether (BDDE).

* * * * *